(12) United States Patent
Winterton et al.

(10) Patent No.: US 6,940,580 B2
(45) Date of Patent: Sep. 6, 2005

(54) POLYMERIC ARTICLES HAVING A LUBRICIOUS COATING AND METHOD FOR MAKING THE SAME

(75) Inventors: Lynn Cook Winterton, Alpharetta, GA (US); Yongxing Qiu, Duluth, GA (US); John Martin Lally, Liburn, GA (US); Manal M. Gabriel, Marietta, GA (US)

(73) Assignee: Novartis AG, Basel (CH)

( * ) Notice: Subject to any disclaimer, the term of this patent is extended or adjusted under 35 U.S.C. 154(b) by 57 days.

(21) Appl. No.: 10/338,631

(22) Filed: Jan. 8, 2003

(65) Prior Publication Data

US 2003/0134132 A1 Jul. 17, 2003

Related U.S. Application Data

(60) Provisional application No. 60/347,116, filed on Jan. 9, 2002.

(51) Int. Cl.$^7$ ................................................ G02C 7/04
(52) U.S. Cl. .................. 352/160 H; 428/508; 428/532; 428/522
(58) Field of Search ................. 351/160 H; 352/160 H; 428/413, 508, 532, 522

(56) References Cited

U.S. PATENT DOCUMENTS

| | | | | |
|---|---|---|---|---|
| 5,135,297 A | * | 8/1992 | Valint, Jr. ............... 351/160 R |
| 5,397,848 A | * | 3/1995 | Yang et al. ................. 525/477 |
| 5,509,899 A | * | 4/1996 | Fan et al. .............. 604/103.14 |
| 5,731,087 A | * | 3/1998 | Fan et al. ................... 428/412 |
| 5,731,095 A | * | 3/1998 | Milco et al. ................ 428/482 |
| 6,340,465 B1 | | 1/2002 | Hsu et al. ................... 424/400 |
| 6,451,871 B1 | | 9/2002 | Winterton et al. .......... 523/106 |
| 6,531,432 B2 | | 3/2003 | Molock et al. ............. 510/112 |
| 6,589,665 B2 | * | 7/2003 | Chabrecek et al. ......... 428/520 |
| 6,699,435 B2 | | 3/2004 | Salpekar et al. .............. 422/40 |
| 2001/0045676 A1 | | 11/2001 | Winterton et al. ........... 264/2.5 |
| 2001/0048975 A1 | | 12/2001 | Winterton et al. ....... 427/412.1 |
| 2002/0086160 A1 | | 7/2002 | Qiu et al. .................... 428/413 |
| 2002/0182265 A1 | | 12/2002 | Burrell et al. ............... 424/618 |
| 2003/0008154 A1 | | 1/2003 | Aguado et al. ............. 428/447 |
| 2003/0052424 A1 | | 3/2003 | Turner et al. .............. 264/1.32 |
| 2003/0125498 A1 | | 7/2003 | McCabe et al. ............... 528/25 |
| 2003/0134132 A1 | * | 7/2003 | Winterton et al. .......... 428/451 |
| 2003/0162862 A1 | | 8/2003 | McCabe et al. ............ 523/106 |

FOREIGN PATENT DOCUMENTS

| | | |
|---|---|---|
| EP | 0 995 762 | 4/2000 |
| JP | 07256844 | 10/1995 |
| WO | WO 90/35520 * | 7/1999 |
| WO | WO 03/066714 | 8/2003 |

OTHER PUBLICATIONS

"Hydrogen–Bonding–Directed Layer–By–Layer Multilayer Assembly: Reconformation Yielding Microporous Films", Fu, Bai, Cui, Qiu, Wang and Zhang, Macromolecules 2002, 35, pp9451–9458.

* cited by examiner

*Primary Examiner*—D. Lawrence Tarazano
(74) *Attorney, Agent, or Firm*—Jian Zhou; Robert Gorman; R. Scott Meece

(57) ABSTRACT

The present invention provides a medical device, preferably an ophthalmic device, more preferably a contact lens, which comprises a lubricious coating including a capping layer of polyvinylpyrrolidone and/or at least one layer of a lubricious coating material and one layer of a polyionic material having charges opposite of the charges of the lubricious coating material. The lubricious coating on the medical device of the invention has increased lubricity, preferably characterized by an averaged CoF of about 3.0 or less, increased hydrophilicity characterized by an averaged contact angle of about 80 degree or less, and increased bacterial adhesion resistance, while maintaining the desired bulk properties such as oxygen permeability and ion permeability of lens material. Such lenses are useful as extended-wear contact lenses. In addition, the invention provides a method for making a medical device, preferably a contact lens, having a lubricious coating thereon.

21 Claims, No Drawings

POLYMERIC ARTICLES HAVING A LUBRICIOUS COATING AND METHOD FOR MAKING THE SAME

This application claims the benefit under 35 U.S.C. §119(e) of U.S. provisional application Ser. No. 60/347,116 filed Jan. 9, 2002, herein incorporated by reference in its entirety.

The present invention generally relates to a medical device having a lubricious coating thereon. In particular, the present invention relates to an ophthalmic lens having a lubricious coating that has high surface hydrophilicity and high lubricity as well as other desired properties such as high oxygen permeability and ion permeability. In addition, this invention provides a method for making a medical device having a lubricious coating.

BACKGROUND OF THE INVENTION

Many devices used in biomedical applications require that the bulk of the device have one property and the surface of the device have a different property. For example, contact lenses may require relatively high oxygen permeability through the bulk of the lens to maintain good corneal health. However, materials that exhibit exceptionally high oxygen permeability (e.g. polysiloxanes) are typically hydrophobic and, untreated or not surface modified, will up take lipid or protein from the ocular environment and may adhere to the eye. Thus, a contact lens will generally have a core or bulk material that is highly oxygen permeable and hydrophobic, and a surface that has been treated or coated to increase hydrophilic properties. This hydrophillic surface allows the lens to move relatively freely on the eye without absorbing excessive amounts of tear lipid and protein.

A known method for modifying the hydrophilicity of a relatively hydrophobic contact lens material is through the use of a plasma treatment. Plasma treatment techniques are disclosed, for example, PCT Publication Nos. WO 96/31793 to Nicholson et al., WO 99/57581 to Chabrececk et al., and WO 94/06485 to Chatelier et al. In the Chabrececk et al. application, photoinitiator molecules are covalently bound to the surface of the article after the article has been subjected to a plasma treatment which provides the surface with functional groups. A layer of polymerizable macromonomer is then coated onto the modified surface and heat or radiation is applied to graft polymerize the macromonomer to form the hydrophilic surface.

Plasma treatment processes, however, require a significant capital investment in plasma processing equipment. Moreover, plasma treatments take place in a vacuum and, thus, require that the substrate be mostly dry before exposure to the plasma. Thus, substrates, such as contact lenses, that are wet from prior hydration or extraction processes must be dried, thereby further adding to both the capital and production costs. As a result of the conditions necessary for plasma treatment, the incorporation of a plasma treatment process into an automated production process is extremely difficult.

Other methods of permanently altering the surface properties of polymeric biomaterials, such as contact lenses, have been developed. Some of these techniques include Langmuir-Blodgett deposition, controlled spin casting, chemisorptions, and vapor deposition. Examples of Langmuir-Blodgett layer systems are disclosed in U.S. Pat. Nos. 4,941,997; 4,973,429; and 5,068,318. Like plasma treatments, these techniques are not cost-effective methods that may easily be incorporated into automated production processes for making biomedical devices such as contact lenses.

A more recent technique developed for coating substrates is a layer-by-layer ("LbL") polymer absorption process, which is described Yoo, et al. ("Investigation of New Self-Assembled Multilayer Thin Films Based on Alternately Adsorbed Layers of Polyelectrolytes and Functional Dye Molecules", Mat. Res. Soc. Symp. Proc. 413: 395–400 (1996)). The process described in this article involves alternatively dipping hydrophilic glass substrates in a polyelectrolyte solution (e.g., polycations such as polyallylamine or polyethyleneimine) and then in an oppositely charged solution to form electrically conducting thin films and light-emitting diodides (LEDs).

A series of three articles described similar LbL polyelectrolyte absorption processes (Ferreira & Rubner, Macromolecules, 28: 7107–7114 (1995); Fou & Rubner, Macromolecules, 28: 7115–7120 (1995); and Cheung et al., Macromolecules, 30:2712–2716 (1997)). These processes involve treating glass substrates that have hydrophilic, hydrophobic, negatively, or positively charged surfaces. The glass surfaces are treated for extended periods in hot acid baths and peroxide/ammonia baths to produce a hydrophilic surface. Hydrophobic surfaces are produced by gas-phase treatment in the presence of 1,1,1,3,3,3-hexamethyldisilazine for 36 hours. Charged surfaces are prepared by covalently anchoring charges onto the surface of the hydrophilic slides. For example, positively charged surfaces are made by further treating the hydrophilic surfaces in methanol, methanol/toluene, and pure toluene rinses, followed by immersion in (N-2 aminoethyl-3-aminopropyl) trimethyloxysilane solution for 12 to 15 hours. This procedure produces glass slides with amine functionalities, which are positively charged at a low pH.

U.S. Pat. Nos. 5,518,767 and 5,536,573 to Rubner et al. describe methods of producing bilayers of p-type doped electrically conductive polycationic polymers and polyanions or water-soluble, non-ionic polymers on glass substrates. These patents describe extensive chemical pretreatments of glass substrates that are similar to those described in the aforementioned articles.

U.S. Pat. No. 5,208,111 to Decher et al. describes a method for applying one or more layers to a support modified by the applications of ions and ionizable compounds of the same charges over the entire area. The one or more layers are made of organic materials which in each layer contain ions of the same charge, the ions of the first layer having the opposite charge of the modified support and in the case of several layers each further layer having again the opposite charge of the previous layer.

U.S. Pat. No. 5,700,559 to Sheu et al. discloses a method for making a hydrophilic article having a substrate, an ionic polymeric layer bonded directly onto the substrate, and a disordered polyelectrolyte coating ionically bonded to the ionic polymeric layer. The ionic polymeric layer is obtained by a plasma treatment, an electron beam treatment, a corona discharge, an X-ray treatment, or an acid/base chemical modification of the substrate.

Although each of the above described surface modification techniques are effective for producing an article with a surface that is different from the remainder of the article, the modification processes requires complex and time-consuming pretreatment of the substrate surface to obtain a highly charged surface.

To overcome this problem, various layer-by-layer (LbL) polyelectrolyte deposition techniques have been developed by the assignee of the present invention (e.g., PCT Publication Nos. WO 01/57118, WO 99/35520). These layer-bylayer techniques effectively alter the surfaces of various materials, such as contact lenses. One such technique is described in U.S. Pat. No. 6,451,871, that involves consecutively dipping a substrate into oppositely charged polyionic materials until a coating of a desired thickness is formed. Another technique that results in a layer-by-layer coating while avoiding the time-consuming aspects of sequential dipping, is the single dip process disclosed in co-pending U.S. patent application Ser. No. 09/775,104 filed on Feb. 1, 2001, entitled "Single-Dip Process for Achieving a Layer-by-Layer-Like Coating", which applies polyionic material onto the substrate with only a single dip. In this technique, a generally hydrophobic article such as a contact lens is dipped into a single polyionic solution containing at least one polycationic material and at least one polyanionic material. The polycationic material may include a positively charged moiety such as poly(allyl amine hydrochloride) and the polyanionic material may include a negatively charged moiety such as polyacrylic acid. Typically, the polyionic components are employed in non-stoichiometric amounts such that one of the components is present within the solution in a greater amount than another component.

Each of these surface modification techniques are effective for producing an article with a surface that is different from the remainder of the article. It would be particularly desirable if such modified surfaces of contact lenses are lubricious and thereby can provide wearers comfort and have minimal adverse effects on the wearer's ocular health and comfort. In addition, it would be also desirable if such surfaces of the contact lenses have low biomaterial-fouling behavior. Such contact lenses may have increased safety as extended-wear contact lenses which could provide comfort, convenience, and safety.

SUMMARY OF THE INVENTION

One object of the invention is to provide a polymeric articles having a lubricious coating, wherein the lubricious coating has relatively high surface hydrophilicity and lubricity, and is capable of reducing bacterial adhesion to the surface of the article.

Another object of the invention is to provide a method for making a polymeric article having a lubricious coating thereon, wherein the lubricious coating has relatively high surface hydrophilicity and lubricity, and is capable of reducing bacterial adhesion to the surface of the article.

These and other objects of the invention are met by the various aspects of the invention described herein.

The invention, in one aspect, provides a polymeric article, preferably an ophthalmic lens, more preferably a contact lens, having a lubricious coating thereon and a surface hydrophilicity characterized by having an averaged contact angle of about 80 degrees or less. The lubricious coating preferably comprises at least one bilayer of a lubricious coating material and a polyionic material having charges opposite of the charges of the lubricious coating material. Preferably, the polymeric article has a low lubricity characterized by having an averaged coefficient of friction of about 3.0 or less. Even more preferably, the polymeric article has an increased bacterial adhesion resistance.

The invention, in another aspect, provides a method of making a polymeric article, preferably, an ophthalmic lens, more preferably a contact lens, having a lubricious coating thereon, wherein the lubricious coating has a high hydrophilicity characterized by a contact angle of about 80 degrees or less and preferably a lubricity characterized by an averaged lubricity/lubricating drag/coefficient of friction of about 3.0 or less. The method of invention comprises applying at least one bilayer of a lubricious material and a polyionic material having charges opposite of the charges of the lubricious material onto the surface of a polymeric article.

These and other aspects of the invention will become apparent from the following description of the presently preferred embodiments. The detailed description is merely illustrative of the invention and does not limit the scope of the invention, which is defined by the appended claims and equivalents thereof. As would be obvious to one skilled in the art, many variations and modifications of the invention may be effected without departing from the spirit and scope of the novel concepts of the disclosure.

DETAILED DESCRIPTION OF PREFERRED EMBODIMENTS

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well known and commonly employed in the art. As employed throughout the disclosure, the following terms, unless otherwise indicated, shall be understood to have the following meanings.

An "article" refers to an ophthalmic lens, a mold for making an ophthalmic lens, or a medical device other than ophthalmic device.

A "medical device", as used herein, refers to a device having surfaces that contact tissue, blood, or other bodily fluids of patients in the course of their operation or utility. Exemplary medical devices include: (1) extracorporeal devices for use in surgery such as blood oxygenators, blood pumps, blood sensors, tubing used to carry blood and the like which contact blood which is then returned to the patient; (2) prostheses implanted in a human or animal body such as vascular grafts, stents, pacemaker leads, heart valves, and the like that are implanted in blood vessels or in the heart; (3) devices for temporary intravascular use such as catheters, guide wires, and the like which are placed into blood vessels or the heart for purposes of monitoring or repair; (4) artificial tissues such as artificial skin for burn patients; (5) dentifices, dental moldings; (6) ophthalmic devices; and (7) cases or containers for storing ophthalmic devices or ophthalmic solutions. In a preferred embodiment, medical devices are ophthalmic devices.

An "ophthalmic device", as used herein, refers to a contact lens (hard or soft), an intraocular lens, a corneal onlay, and other ophthalmic devices (e.g., stents, glaucoma shunt, or the like) used on or about the eye or ocular vicinity.

The "outer surface" of a lens, as used herein, refers to the surface of the lens which faces away from the eye during wear. The outer surface, which is typically substantially convex, may also be referred to as the front curve of the lens. The "inner surface" of a lens, as used herein, refers to the surface of the lens which faces towards the eye during wear. The inner surface, which is typically substantially concave, may also be referred to as the base curve of the lens.

"Ophthalmically compatible", as used herein, refers to a material or surface of a material which may be in intimate contact with the ocular environment for an extended period of time without significantly damaging the ocular environment and without significant user discomfort. Thus, an ophthalmically compatible contact lens will not produce significant corneal swelling, will adequately move on the eye with blinking to promote adequate tear exchange, will not have substantial amounts of protein or lipid adsorption, and will not cause substantial wearer discomfort during the prescribed period of wear.

"Ocular environment", as used herein, refers to ocular fluids (e.g., tear fluid) and ocular tissue (e.g., the cornea) which may come into intimate contact with a contact lens used for vision correction, drug delivery, wound healing, eye color modification, or other ophthalmic applications.

A "monomer" means a low molecular weight compound that can be polymerized. Low molecular weight typically means average molecular weights less than 700 Daltons.

A "macromer" refers to medium and high molecular weight compounds or polymers that contain functional groups capable of further polymerization. Medium and high molecular weight typically means average molecular weights greater than 700 Daltons.

"Polymer" means a material formed by polymerizing one or more monomers.

"Surface modification", as used herein, refers to treating an article to alter its surface properties. For example, an article can be treated in a surface treatment process (or a surface modification process), in which, by means of contact with a vapor or liquid, and/or by means of application of an energy source (1) a coating is applied to the surface of an article, (2) chemical species are adsorbed onto the surface of an article, (3) the chemical nature (e.g., electrostatic charge) of chemical groups on the surface of an article are altered, or (4) the surface properties of an article are otherwise modified. Exemplary surface treatment processes include, but are not limited to, a surface treatment by energy (e.g., a plasma, a static electrical charge, irradiation, or other energy source), chemical treatments, the grafting of hydrophilic monomers or macromers onto the surface of an article, and layer-by-layer deposition of polyelectrolytes. A preferred class of surface treatment processes are plasma processes, in which an ionized gas is applied to the surface of an article. Plasma gases and processing conditions are described more fully in U.S. Pat. Nos. 4,312,575 and 4,632,844, which are incorporated herein by reference. The plasma gas is preferably a mixture of lower alkanes and nitrogen, oxygen or an inert gas. The surface modification of a contact lens includes, without limitation, the grafting of monomers or macromers onto polymers to make the lens biocompatible, deposit resistant, more hydrophilic, more hydrophobic, or the deposing of polyionic materials (LbL coating) to increase the lens hydrophilic properties or lubricity or to reduce bacterial adhesion or to impart antimicrobial or antifungal properties.

"LbL coating", as used herein, refers to a coating obtained by a layer-by-layer ("LbL") alternative, physical deposition of two oppositely charged polymeric materials (polyionic materials) on an article. An LbL coating is not covalently attached to the core material of an article. In an LbL coating, each layer of a polyionic material is non-covalently bond to another layer of a different polyionic material. Any suitable deposition techniques can be used in the LbL coating. Any suitable LbL polyelectrolyte deposition techniques can be used in the LbL coating. One such technique is described in U.S. Pat. No. 6,451,871, that involves consecutively dipping a substrate into oppositely charged polyionic materials until a coating of a desired thickness is formed. Another such technique that results in a layer-by-layer coating while avoiding the time-consuming aspects of sequential dipping, is the single dip process disclosed in co-pending U.S. patent application Ser. No. 09/775,104 filed on Feb. 1, 2001, entitled "Single-Dip Process for Achieving a Layer-by-Layer-Like Coating", which applies polyionic material onto the substrate with only a single dip.

As used herein, a "polyionic material" refers to a polymeric material that has a plurality of charged groups, such as polyelectrolytes, p- and n-type doped conducting polymers. Polyionic materials include both polycationic (having positive charges) and polyanionic (having negative charges) materials.

As used herein, "asymmetrical coatings" on an ophthalmic lens refers to the different coatings on the first surface and the opposite second surface of the ophthalmic lens. As used herein, "different coatings" refers to two coatings that have different surface properties or functionalities.

A "capping layer", as used herein, refers to the last layer of a coating material which is applied onto the surface of a medical device.

A "polyquat", as used herein, refers to a polymeric quaternary ammonium group-containing compound.

The "oxygen transmissibility" of a lens, as used herein, is the rate at which oxygen will pass through a specific ophthalmic lens. Oxygen transmissibility, Dk/t, is conventionally expressed in units of barrers/mm, where t is the average thickness of the material [in units of mm] over the area being measured and "barrer/mm" is defined as:

$$[(cm^3 \ oxygen)/(cm^2)(sec)(mmHg)] \times 10^{-9}$$

The "oxygen permeability", Dk, of a lens material does not depend on lens thickness. Oxygen permeability is the rate at which oxygen will pass through a material. Oxygen permeability is conventionally expressed in units of barrers, where "barrer" is defined as:

$$[(cm^3 \ oxygen)(mm)/(cm^2)(sec)(mmHg)] \times 10^{-10}$$

These are the units commonly used in the art. Thus, in order to be consistent with the use in the art, the unit "barrer" will have the meanings as defined above. For example, a lens having a Dk of 90 barrers ("oxygen permeability barrers") and a thickness of 90 microns (0.090 mm) would have a Dk/t of 100 barrers/mm (oxygen transmissibility barrers/mm).

The "ion permeability" through a lens correlates with both the Ionoflux Diffusion Coefficient and the Ionoton Ion Permeability Coefficient.

The Ionoflux Diffusion Coefficient, D, is determined by applying Fick's law as follows:

$$D = -n'/(A \times dc/dx)$$

where n'=rate of ion transport [mol/min]
A=area of lens exposed [mm$^2$]
D=Ionoflux Diffusion Coefficient[mm$^2$/min]
dc=concentration difference [mol/L]
dx=thickness of lens [mm]

The Ionoton Ion Permeability Coefficient, P, is then determined in accordance with the following equation:

$$\ln(1 - 2C(t)/C(0)) = -2APt/Vd$$

where: C(t)=concentration of sodium ions at time t in the receiving cell
C(0)=initial concentration of sodium ions in donor cell
A=membrane area, i.e., lens area exposed to cells
V=volume of cell compartment (3.0 ml)
d=average lens thickness in the area exposed
P=permeability coefficient An Ionoflux Diffusion Coefficient, D, of greater than about 0.2×10$^{-3}$ mm$^2$/min is preferred, while greater than about 0.64×10$^{-3}$ mm$^2$/min is more preferred and greater than about 1.0×10$^{-3}$ mm$^2$/min is most preferred.

A "lubricious coating" refers to a coating that can impart increased surface hydrophilicity and increased lubricity.

An "averaged value of lubricity/lubricating drag/coefficient of friction" refers to a value, which is obtained by averaging measurements of at least 3 individual medical devices, as described in Example 10. Lubricity/lubricating drag/coefficient of friction (hereinafter CoF) may be one of important parameters that may affect the on-eye movement and thereby the wearer's comfort. High CoF may increase the likelihood of damaging mechanically the ocular epithelia and/or may lead to ocular discomfort.

As used herein, "increased lubricity" in reference to a coated contact lens means that the coated contact lens has a reduced averaged value of CoF relative to a uncoated contact lens, wherein both coated and uncoated contact lenses are made of the same core material.

An "average contact angle" refers to a contact angle (measured by Sessile Drop method), which is obtained by averaging measurements of at least 3 individual medical devices.

As used herein, "increased surface hydrophilicity" or "increased hydrophilicity" in reference to a coated ophthalmic device means that the coated ophthalmic device has a reduced averaged contact angle.

As used herein, "increased bacterial-adhesion resistance in reference to a coated contact lens means that, after inoculating with an inoculum of about 1.0×10$^8$ CFU/ml *P. aeruginosa* GSU # 3, the coated contact lens has a reduced value of Colony Forming Units (CFU/mm$^2$) per the surface area relative to an uncoated contact lens made of the same core material. Preferably, the value of Colony Forming Units (CFU/mm$^2$) per the surface area of a coated contact lens is at least about one order lower than that of an uncoated lens.

In general, the present invention is directed to a medical device having a core material and a lubricious surface coating (hereinafter lubricious coating) formed thereon and a surface hydrophilicity characterized by having an average contact angle of about 80 degrees or less. Preferably, the lubricious coating has an average CoF of about 3.0 or less and/or an increased bacterial adhesion resistance characterized by having a value of Colony Forming Units (CFU/mm$^2$) per the surface area that is at least about one order lower than that of an uncoated lens.

In particular, the present invention is directed to a medical device, preferably an ophthalmic lens, more preferably a contact lens, having a lubricious coating comprising a capping layer of polyvinylpyrrolidone or at least one lubricious bilayer which is composed of one layer of the lubricious coating material and one layer of a polyionic material having charges opposite of the charges of the lubricious coating material.

The term "bilayer" is employed herein in a broad sense and is intended to encompass, a coating structure formed by applying first one layer of a first polyionic material and then one layer of a second polyionic material having charges opposite of the first polyionic material. Where one of the first and second polyionic materials is a lubricious coating material, the bilayer is referred to a lubricious bilayer. It should be understood that the layers of the first and second polyionic materials may be intertwined with each other in the bilayer.

The lubricious coating material can be a polyionic material selected from the group consisting of hyaluronic acid and salts thereof, glycosaminoglycanes (e.g., heparin or chondroitin sulfate), fucoidan, poly-aspartic acid, poly-glutamic acid, carboxymethyl cellulose, carboxymethyl dextranes, alginates, pectins, gellan, carboxyalkyl chitins, carboxymethyl chitosans, sulfated polysaccharides, glucoproteins (e.g., poly-ϵ-lysine, albumin or collagen), aminoalkylated polysaccharides (e.g., chitosans or aminodextranes), Starburst® polyamidoamine (PAMAM) dendrimers (Aldrich), PAAm-co-PAA.

Preferably, the lubricious coating material is selected from the group consisting of alginates, PAH lactone, hyaluronic acid and salts thereof, Starburst® polyamidoamine (PAMAM) dendrimers (Aldrich), PAAm-co-PAA, chondroitin sulfate, chitosan, proteoglycans, proteoglycan mimics, and mixtures thereof.

The polyionic materials that may be employed in the present invention include polyanionic and polycationic polymers. Examples of suitable polyanionic polymers include, for example, a synthetic polymer, a biopolymer or modified biopolymer comprising carboxy, sulfo, sulfato, phosphono or phosphato groups or a mixture thereof, or a salt thereof, for example, a biomedical acceptable salt and especially an ophthalmically acceptable salt thereof when the article to be coated is an ophthalmic device.

Examples of synthetic polyanionic polymers are: a linear polyacrylic acid (PAA), a branched polyacrylic acid, for example a Carbophil® or Carbopol® type from Goodrich Corp., a poly-methacrylic acid (PMA), a polyacrylic acid or polymethacrylic acid copolymer, for example a copolymer of acrylic or methacrylic acid and a further vinylmonomer, for example acrylamide, N,N-dimethyl acrylamide or N-vinylpyrrolidone, a maleic or fumaric acid copolymer, a poly(styrene-sulfonic acid) (PSS), a polyamido acid, for example a carboxy-terminated polymer of a diamine and a di- or polycarboxylic acid, for example carboxy-terminated Starburst® polyamidoamine (PAMAM) dendrimers (Aldrich), a poly(2-acrylamido-2-methylpropanesulfonic acid) (poly-(AMPS)), or an alkylene polyphosphate, alkylene polyphosphonate, carbohydrate polyphosphate or carbohydrate polyphosphonate, for example a teichoic acid.

Examples of polyanionic biopolymers or modified biopolymers are: hyaluronic acid, glycosaminoglycanes such as heparin or chondroitin sulfate, fucoidan, poly-aspartic acid, poly-glutamic acid, carboxymethyl cellulose, carboxymethyl dextranes, alginates, pectins, gellan, carboxyalkyl chitins, carboxymethyl chitosans, sulfated polysaccharides.

A preferred polyanionic polymer is a linear or branched polyacrylic acid or an acrylic acid copolymer. A more preferred anionic polymer is a linear or branched polyacrylic acid. A branched polyacrylic acid in this context is to be understood as meaning a polyacrylic acid obtainable by polymerizing acrylic acid in the presence of suitable (minor) amounts of a di- or polyvinyl compound.

A suitable polycationic polymer as part of the bilayer is, for example, a synthetic polymer, biopolymer or modified biopolymer comprising primary, secondary or tertiary amino groups or a suitable salt thereof, preferably an ophthalmically acceptable salt thereof, for example a hydrohalogenide such as a hydrochloride thereof, in the backbone or as substituents. Polycationic polymers comprising primary or secondary amino groups or a salt thereof are preferred.

Examples of synthetic polycationic polymers are:
(i) a polyallylamine (PAH) homo- or copolymer, optionally comprising modifier units;
(ii) a polyethyleneimine (PEI);
(iii) a polyvinylamine homo- or copolymer, optionally comprising modifier units;
(iv) a poly(vinylbenzyl-tri-$C_1$–$C_4$-alkylammonium salt), for example a poly(vinylbenzyl-tri-methyl ammoniumchloride);
(v) a polymer of an aliphatic or araliphatic dihalide and an aliphatic N,N,N',N'-tetra-$C_1$–$C_4$-alkyl-alkylenediamine, for example a polymer of (a) propylene-1,3-dichloride or -dibromide or p-xylylene dichloride or dibromide and (b) N,N,N',N'-tetramethyl-1,4-tetramethylene diamine;
(vi) a poly(vinylpyridine) or poly(vinylpyridinium salt) homo- or copolymer;
(vii) a poly (N,N-diallyl-N,N-di-$C_1$–$C_4$-alkyl-ammoniumhalide) comprising units of formula

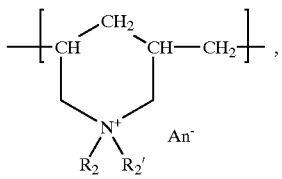

wherein $R_2$ and $R_2'$ are each independently $C_1$–$C_4$-alkyl, in particular methyl, and $An^-$ is an anion, for example, a halide anion such as the chloride anion;
(viii) a homo- or copolymer of a quaternized di-$C_1$–$C_4$-alkyl-aminoethyl acrylate or methacrylate, for example a poly(2-hydroxy-3-methacryloylpropyltri-$C_1$–$C_2$-alkylammonium salt) homopolymer such as a a poly(2-hydroxy-3-methacryloylpropyltri-methylammonium chloride), or a quaternized poly(2-dimethylaminoethyl methacrylate or a quaternized poly(vinylpyrrolidone-co-2-dimethylaminoethyl methacrylate);
(ix) POLYQUAD® as disclosed in EP-A-456,467; or
(x) a polyaminoamide (PAMAM), for example a linear PAMAM or a PAMAM dendrimer such as an amino-terminated Starbust™ PAMAM dendrimer (Aldrich).

The above mentioned polymers comprise in each case the free amine, a suitable salt thereof, for example a biomedically acceptable salt or in particular an ophthalmically acceptable salt thereof, as well as any quaternized form, if not specified otherwise.

Suitable comonomers optionally incorporated in the polymers according to (i), (iii), (vi) or (viii) above are, for example, hydrophilic monomers such as acrylamide, methacrylamide, N,N-dimethyl acrylamide, N-vinylpyrrolidone and the like.

Suitable modifier units of the polyallylamine (i) are known, for example from WO 00/31150 and comprise, for example, units of formula

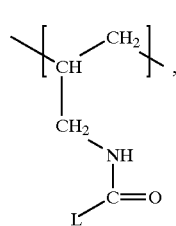

(1)

wherein L is $C_2$–$C_6$-alkyl which is substituted by two or more same or different substituents selected from the group consisting of hydroxy, $C_2$–$C_5$-alkanoyloxy and $C_2$–$C_5$-alkylamino-carbonyloxy.

Preferred substituents of the alkyl radical L are hydroxy, acetyloxy, propionyloxy, methylaminocarbonyloxy or ethylaminocarbonyloxy, especially hydroxy, acetyloxy or propionyloxy and in particular hydroxy.

L is preferably linear $C_3$–$C_6$-alkyl, more preferably linear $C_4$–$C_5$-alkyl, and most preferably n-pentyl, which is in each case substituted as defined above. A particularly preferred radical L is 1,2,3,4,5-pentahydroxy-n-pentyl.

Examples of polycationic biopolymers or modified biopolymers that may be employed in the bilayer of the present invention include: basic peptides, proteins or glucoproteins, for example, a poly-ε-lysine, albumin or collagen, aminoalkylated polysaccharides such as a chitosan or aminodextranes.

Particular polycationic polymers for forming the bilayer of the present invention include a polyallylamine homopolymer; a polyallylamine comprising modifier units of the above formula (1); a polyvinylamine homo- or -copolymer or a polyethyleneimine homopolymer, in particular a polyallylamine or polyethyleneimine homopolymer, or a poly (vinylamine-co-acrylamid) copolymer.

The foregoing lists are intended to be exemplary, but clearly are not exhaustive. A person skilled in the art, given the disclosure and teaching herein, would be able to select a number of other useful polyionic materials.

In order to alter various characteristics of the coating, such as thickness, the molecular weight of the polyionic materials including polyquats can be varied. In particular, as the molecular weight is increased, the coating thickness generally increases. However, if the increase in molecular weight increase is too substantial, the difficulty in handling may also increase. As such, polyionic materials used in a process of the present invention will typically have a molecular weight $M_n$ of about 2,000 to about 150,000. In some embodiments, the molecular weight is about 5,000 to about 100,000, and in other embodiments, from about 75,000 to about 100,000.

In accordance with the present invention, the core material of a medical device may be any of a wide variety of polymeric materials. Exemplary core materials include, but are not limited to, hydrogels, silicone-containing hydrogels, polymers and copolymers of styrene and substituted styrenes, ethylene, propylene, acrylates and methacrylates, N-vinyl lactams, acrylamides and methacrylamides, acrylonitrile, acrylic and methacrylic acids.

A preferred group of core materials to be coated are those being conventionally used for the manufacture of biomedical devices, e.g. contact lenses, in particular contact lenses for extended wear, which are not hydrophilic per se. Such materials are known to the skilled artisan and may comprise for example polysiloxanes, perfluoroalkyl polyethers, fluorinated poly(meth)acrylates or equivalent fluorinated polymers derived e.g. from other polymerizable carboxylic acids, polyalkyl (meth)acrylates or equivalent alkylester polymers derived from other polymerizable carboxylic acids, or fluorinated polyolefines, such as fluorinated ethylene or propylene, for example tetrafluoroethylene, preferably in combination with specific dioxols, such as perfluoro-2,2-dimethyl-1,3-dioxol. Examples of suitable bulk materials are e.g. Lotrafilcon A, Neofocon, Pasifocon, Telefocon, Silafocon, Fluorsilfocon, Paflufocon, Silafocon, Elastofilcon, Fluorofocon or Teflon AF materials, such as Teflon AF 1600 or Teflon AF 2400 which are copolymers of about 63 to 73 mol % of perfluoro-2,2-dimethyl-1,3-dioxol and about 37 to 27 mol % of tetrafluoroethylene, or of about 80 to 90 mol % of perfluoro-2,2-dimethyl-1,3-dioxol and about 20 to 10 mol % of tetrafluoroethylene.

Another group of preferred core materials to be coated is amphiphilic segmented copolymers comprising at least one hydrophobic segment and at least one hydrophilic segment which are linked through a bond or a bridge member. Examples are silicone hydrogels, for example those disclosed in PCT applications WO 96/31792 to Nicolson et al. and WO 97/49740 to Hirt et al.

A particular preferred group of core materials to be coated comprises organic polymers selected from polyacrylates, polymethacrylates, polyacrylamides, poly(N,N-dimethylacrylamides), polymethacrylamides, polyvinyl acetates, polysiloxanes, perfluoroalkyl polyethers, fluorinated polyacrylates or -methacrylates and amphiphilic segmented copolymers comprising at least one hydrophobic segment, for example a polysiloxane or perfluoroalkyl polyether segment or a mixed polysiloxane/perfluoroalkyl polyether segment, and at least one hydrophilic segment, for example a polyoxazoline, poly(2-hydroxyethylmethacrylate), polyacrylamide, poly(N,N-dimethylacrylamide), polyvinylpyrrolidone polyacrylic or polymethacrylic acid segment or a copolymeric mixture of two or more of the underlying monomers.

The core material to be coated may also be any blood-contacting material conventionally used for the manufacture of renal dialysis membranes, blood storage bags, pacemaker leads or vascular grafts. For example, the material to be modified on its surface may be a polyurethane, polydimethylsiloxane, polytetrafluoroethylene, polyvinylchloride, Dacron™ or Silastic™ type polymer, or a composite made therefrom.

An lubricious coating of the present invention may find particular use in extended-wear contact lenses. The lubricious coating of the invention may have a minimal adverse effects on the desirable bulk properties of the lens, such as oxygen permeability, ion permeability, and optical properties.

Another embodiment of the invention is a method for producing a medical device having a core material and a lubricious coating comprising at least one layer of lubricious coating material and one layer of a polyionic material having charges opposite of the charges of the lubricious coating material. The method of the invention comprises applying alternatively, in no particular order, one layer of lubricious coating material and one layer of a polyionic material having charges opposite of the charges of the lubricious coating material, using a layer-by-layer polyelectrolyte deposition technique.

It has been discovered and disclosed in U.S. Pat. No. 6,451,871 that complex and time-consuming pretreatment of a core material (medical device) is not required prior to binding of a polyionic material to the core material. By simply contacting a core material of a medical device, for example, a contact lens, with one or more solutions each containing one or more polyionic materials, an LbL coating can be formed on a medical device to modify the surface properties of the core material of the medical device.

Application of an LbL coating may be accomplished in a number of ways as described in U.S. Pat. No. 6,451,871 and pending U.S. patent applications (appl. Ser. Nos. 09/199,609, 09/559,945, 09/775,104), herein incorporated by reference in their entireties. One coating process embodiment involves solely dip-coating and dip-rinsing steps. Another coating process embodiment involves solely spray-coating and spray-rinsing steps. However, a number of alternatives involve various combinations of spray- and dip-coating and rinsing steps may be designed by a person having ordinary skill in the art.

One dip-coating alternative involves the steps of applying a coating of a first polyionic material to a core material of a medical device by immersing said medical device in a first solution of a first polyionic material; rinsing the medical device by immersing the medical device in a rinsing solution; and, optionally, drying the medical device. This procedure can be repeated using a second polyionic material, with the second polyionic material having charges opposite of the charges of the first polyionic material, in order to form a polyionic bilayer. This bilayer formation process may be repeated a plurality of times in order to produce a thicker LbL coating. A preferred number of bilayers is about 5 to about 20 bilayers. While more than 20 bilayers are possible, it has been found that delamination may occur in some LbL coatings having an excessive number of bilayers.

The immersion time for each of the coating and rinsing steps may vary depending on a number of factors. Preferably, immersion of the core material into the polyionic solution occurs over a period of about 1 to 30 minutes, more preferably about 2 to 20 minutes, and most preferably about 1 to 5 minutes. Rinsing may be accomplished with a plurality of rinsing steps, but a single rinsing step can be quite efficient.

Another embodiment of the coating process is a single dip-coating process as described in U.S. application Ser. No. 09/775,104, herein incorporated by reference in its entirety. Such single dip-coating process involves dipping a core material of a medical device in a solution containing a negatively charged polyionic material and a positively charged polyionic material in an amount such that the molar charge ratio of said solution is from about 3:1 to about 100:1. Multiple bilayers can be formed on a medical device by using this single dip-coating process.

Another embodiment of the coating process involves a series of spray coating techniques. The process generally includes the steps of applying a coating of a first polyionic material to a core material of a medical device with a first solution of a first polyionic material; rinsing the medical device by spraying the medical device with a rinsing solution; and optionally, drying the medical device. Similar to the dip-coating process, the spray-coating process may be repeated with a second polyionic material, with the second polyionic material having charges opposite of the charges of the first polyionic material.

The contacting of the medical device with solution, either polyionic material or rinsing solution, may occur by a variety of methods. For example, the medical device may be dipped into both solutions. One preferred alternative is to apply the solutions in a spray or mist form. Of course, various combinations may be envisioned, e.g., dipping the medical device in the polyionic material followed by spraying the rinsing solution.

The spray coating application may be accomplished via a number of methods. For example, a conventional spray coating arrangement may be used, i.e., the liquid material is sprayed by application of fluid, which may or may not be at elevated pressure, through a reduced diameter nozzle which is directed towards the deposition target.

Preferably, a spraying process is selected from the group consisting of an air-assisted atomization and dispensing process, an ultrasonic-assisted atomization and dispensing process, a piezoelectric assisted atomization and dispensing process, an electro-mechanical jet printing process, a piezo-electric jet printing process, a piezo-electric with hydrostatic pressure jet printing process, and a thermal jet printing process; and a computer system capable of controlling the positioning of the dispensing head of the spraying device on the ophthalmic lens and dispensing the coating liquid. Those spraying coating processes are described in U.S. application Ser. No. 10/154,249, entitled "Method and Apparatus for Applying a coating to an ophthalmic lens" filed May 22, 2002, herein incorporated by reference in its entirety. By using such spraying coating processes, an asymmetrical coating can be applied to a medical device. For example, the back surface of a contact lens can be coated with a hydrophilic and/or lubricous coating material and the front surface of the contact lens can be coated with an antimicrobial material. It is also possible to produce a coating on a contact lens, the coating having a functional pattern so as to provide simultaneously multiple benefits to a wearer.

In accordance with the present invention, polyionic material solutions can be prepared in a variety of ways. In particular, a polyionic solution of the present invention can be formed by dissolving the polyionic material(s) in water or any other solvent capable of dissolving the materials. When a solvent is used, any solvent that can allow the components within the solution to remain stable in water is suitable. For example, an alcohol-based solvent can be used. Suitable alcohols can include, but are not limited to, isopropyl alcohol, hexanol, ethanol, etc. It should be understood that other solvents commonly used in the art can also be suitably used in the present invention.

Whether dissolved in water or in a solvent, the concentration of a polyionic material in a solution of the present invention can generally vary depending on the particular materials being utilized, the desired coating thickness, and a number of other factors. However, it may be typical to formulate a relatively dilute aqueous solution of polyionic material. For example, a polyionic material concentration can be between about 0.0001% to about 0.25% by weight, between about 0.005% to about 0.10% by weight, or between about 0.01% to about 0.05% by weight.

In general, the polyionic solutions mentioned above can be prepared by any method well known in the art for preparing solutions. For example, in one embodiment, a polyanionic solution can be prepared by dissolving a suitable amount of the polyanionic material, such as polyacrylic acid having a molecular weight of about 90,000, in water such that a solution having a certain concentration is formed. In one embodiment, the resulting solution is a 0.001M PAA solution. Once dissolved, the pH of the polyanionic solution can also be adjusted by adding a basic or acidic material. In the embodiment above, for example, a suitable amount of 1N hydrochloric acid (HCl) can be added to adjust the pH to 2.5.

Polycationic solutions can also be formed in a manner as described above. For example, in one embodiment, poly (allylamine hydrochloride) having a molecular weight of about 50,000 to about 65,000 can be dissolved in water to form a 0.001M PAH solution. Thereafter, the pH can also be adjusted to 2.5 by adding a suitable amount of hydrochloric acid.

In some embodiments of the present invention, it may be desirable to apply a solution containing both polyanionic and polycationic materials within a single solution. For example, a polyanionic solution can be formed as described above, and then mixed with a polycationic solution that is also formed as described above. In one embodiment, the solutions can then be mixed slowly to form the coating solution. The amount of each solution applied to the mix depends on the molar charge ratio desired. For example, if a 10:1 (polyanion:polycation) solution is desired, 1 part (by volume) of the PAH solution can be mixed into 10 parts of the PAA solution. After mixing, the solution can also be filtered if desired.

A medical device of the invention can also be made by first applying a lubricious coating to a mold for making a medical device and then transfer-grafting the lubricious coating to the medical device made from the mold, in substantial accordance with the teachings of U.S. patent application (Ser. No. 09/774,942), herein incorporated by reference in its entirety.

Methods of forming mold sections for cast-molding a contact lens are generally well known to those of ordinary skill in the art. The process of the present invention is not limited to any particular method of forming a mold. In fact, any method of forming a mold can be used in the present invention. However, for illustrative purposes, the following discussion has been provided as one embodiment of forming a mold on which a color image can be printed in accordance with the present invention.

In general, a mold comprises at least two mold sections (or portions) or mold halves, i.e. first and second mold halves. The first mold half defines a first optical surface and the second mold half defines a second optical surface. The first and second mold halves are configured to receive each other such that a contact lens forming cavity is formed between the first optical surface and the second optical surface. The first and second mold halves can be formed through various techniques, such as injection molding. These half sections can later be joined together such that a contact lens-forming cavity is formed therebetween. Thereafter, a contact lens can be formed within the contact lens-forming cavity using various processing techniques, such as ultraviolet curing.

Examples of suitable processes for forming the mold halves are disclosed in U.S. Pat. No. 4,444,711 to Schad; U.S. Pat. No. 4,460,534 to Boehm et al.; U.S. Pat. No. 5,843,346 to Morrill; and U.S. Pat. No. 5,894,002 to Boneberger et al., which are also incorporated herein by reference.

Virtually all materials known in the art for making molds can be used to make molds for making contact lenses. For example, polymeric materials, such as polyethylene, polypropylene, and PMMA can be used. Other materials that allow UV light transmission could be used, such as quartz glass.

Once a mold is formed, a transferable lubricious coating, which comprises at least one layer of a lubricious coating material, can be applied onto the optical surface (inner surface) of one or both mold portions by using the above-described LbL deposition techniques. The inner surface of a mold portion is the cavity-forming surface of the mold and in direct contact with lens-forming material. A transferable lubricious coating can be applied onto the mold portion defining the posterior (concave) surface of a contact lens or on the mold section defining the anterior surface of a contact lens or on both mold portions.

Once a transferable lubricious coating is applied onto the optical surface of one or both mold portions, a lens material can then be dispensed into the contact lens forming cavity defined by the assembled mold halves. In general, a lens material can be made from any polymerizable composition. In particular, when forming a contact lens, the lens material may be an oxygen-permeable material, such as fluorine- or siloxane-containing polymer. For example, some examples of suitable substrate materials include, but are not limited to, the polymeric materials disclosed in U.S. Pat. No. 5,760,100 to Nicolson et al., which is incorporated herein by reference. The lens material can then be cured, i.e. polymerized, within the contact lens-forming cavity to form the contact lens, whereby at least a portion of the transferable coating detaches from the optical surface and reattaches to the formed contact lens.

Thermal curing or photo curing methods can be used to curing a polymerizable composition in a mold to form an ophthalmic lens. Such curing methods are well-known to a person skilled in the art.

In addition to polyionic materials, a coating solution for forming the bilayer or part of it, can also contain additives. As used herein, an additive can generally include any chemical or material. For example, active agents, such as antimicrobials and/or antibacterials can be added to a solution forming the bilayer, particularly when used in biomedical applications. Some antimicrobial polyionic materials include polyquaternary ammonium compounds, such as those described in U.S. Pat. No. 3,931,319 to Green et al. (e.g. POLYQUAD®).

Moreover, other examples of materials that can be added to a coating solution are polyionic materials useful for ophthalmic lenses, such as materials having radiation absorbing properties. Such materials can include, for example, visibility tinting agents, iris color modifying dyes, and ultraviolet (UV) light tinting dyes.

Still another example of a material that can be added to a coating solution is a polyionic material that inhibits or induces cell growth. Cell growth inhibitors can be useful in devices that are exposed to human tissue for an extended time with an ultimate intention to remove (e.g. catheters or Intra Ocular Lenses (IOL's), where cell overgrowth is undesirable), while cell growth-inducing polyionic materials can be useful in permanent implant devices (e.g. artificial cornea).

When additives are applied to a coating solution, such additives, preferably, have a charge. By having a positive or negative charge, the additive can be substituted for one of the polyionic materials in solution at the same molar ratio. For example, polyquaternary ammonium compounds typically have a positive charge. As such, these compounds can be substituted into a solution of the present invention for the polycationic component such that the additive is applied to the core material of an article in a manner similar to how a polycationic would be applied.

It should be understood, however, that non-charged additives can also be applied to the core material of an article. For example, in one embodiment, a polycationic layer can first applied onto the core material of the article. Thereafter, a non-charges additive can be applied and immediately entrapped by a polyanionic material applied thereon. In this embodiment, the polyanionic material can sufficiently entrap the non-charged additive between two or more layers of polyionic material. After such entrapment, the article can then be coated with other layers of polyionic materials in accordance with the present invention.

Moreover, the core material to be coated may also be an inorganic or metallic base material without suitable reactive groups, e.g. ceramic, quartz, or metals, such as silicon or gold, or other polymeric or non-polymeric substrates. e.g., for implantable biomedical applications, ceramics are very useful. In addition, e.g. for biosensor purposes, hydrophilically coated base materials are expected to reduce nonspecific binding effects if the structure of the coating is well controlled. Biosensors may require a specific carbohydrate coating on gold, quartz, or other non-polymeric substrates.

The form of the material to be coated may vary within wide limits. Examples are particles, granules, capsules, fibers, tubes, films or membranes, preferably moldings of all kinds such as ophthalmic moldings, for example intraocular lenses, artificial cornea or in particular contact lenses.

The previous disclosure will enable one having ordinary skill in the art to practice the invention. In order to better enable the reader to understand specific embodiments and the advantages thereof, reference to the following examples is suggested.

EXAMPLE 1

Contact Lenses Having an LbL Coating with a Capping Layer of Polyvinylpyrrolidone (PVP)

Polyacrylic acid (PAA) solution: A solution of polyacrylic acid having a molecular weight of about 90,000, from PolyScience, is prepared by dissolving a suitable amount of the material in water to form a 0.001M PAA solution. The PAA concentration is calculated based on the repeating unit in PAA. Once dissolved, the pH of the polyanionic PAA solution is adjusted by adding 1N hydrochloric acid until the pH is about 2.5.

Poly(allylamine hydrochloride) (PAH) solution: A solution of poly(allylamine hydrochloride) (PAH) having a molecular weight of about 70,000, from Aldrich, is prepared by dissolving a suitable amount of the material in water to form a 0.001M PAH solution. The concentration is calculated based on the molecular weight of repeating unit in PAH. Thereafter, the pH of the polycationic PAH solution is measured and recorded. The pH is around 4.5

Polyvinylpyrrolidone (PVP) solution: A solution of polyvinylpyrrolidone (PVP, from Aldrich) having a molecular weight of 50,000 is prepared by dissolving a suitable amount of the material in water to form a 0.01M PVP solution. The concentration is calculated based on the repeating unit in PVP. Once dissolved, the pH of the PVP solution is adjusted by adding 1N hydrochloric acid until the pH is about 2.5.

Coating: A coating having a capping layer of PVP is formed on a soft contact lens made of a fluorosiloxane hydrogel material, lotrafilcon A (CIBA Vision). Initially, a contact lens is dipped in the PAA solution (0.001M, pH2.5) for 30 minutes, then dipped in the PAH solution (0.001M, approx pH 4.0) for 5 minutes, rinsed with ultra-pure water for 1 minute, then dipped in the PAA solution for 5 minutes, rinsed with ultra-pure water for 1 minute. The 5 minute dipping and 1 minute rinsing steps are repeated for about from 9 to 20 times to apply alternatively layers of PAA and PAH with an outer layer of PAA. Then the lens is dipped in the PVP solution for 5 minutes, followed by two 1-minute water rinsing steps. The lens is then packaged in saline and sterilized.

EXAMPLE 2

Contact Lenses Having Multiple Bilayers of Polyamidoamine (PAMAM) Dendrimer/ polyacrylamide-co-poly(Acrylic Acid) Copolymer (PAAm-co-PAA) Thereon PAA and PAH solutions: PAA and PAH solutions are prepared as described in Example 1.

Starburst PAMAM dendrimer solution: A solution of Starburst™ PAMAM dendrimer (from Dentritech, Inc) having generation 4.0 is prepared by dissolving a suitable amount of the material in water to form a 0.001M PAMAM solution. The PAMAM dendrimer concentration is calculated based on the average molecular weight of dendrimer-forming unit per amino group. Once dissolved, the pH of the PAMAM solution is adjusted by adding 1N hydrochloric acid until a desired pH.

PAAm-co-PAA solution: A solution of PAAm-co-PAA copolymer (80% PAAm ad 20% PAA, from Advanced Research Unit, Ciba Vision Switzerland) is prepared by dissolving a suitable amount of the material in water to form a 0.001M solution. The PAAm-co-PAA copolymer concentration is calculated based on the molecualr weight of repeat unit. Once dissolved, the pH of the PAAm-co-PAA solution is adjusted by adding 1N hydrochloric acid until desired pH Coating A: A coating having multiple bilayers of PAMAM/PAAm-co-PAA is formed on a soft contact lens made of a fluorosiloxane hydrogel material, lotrafilcon A (CIBA Vision). The contact lens is dipped in the PAA solution (0.001M, pH 2.5) for 30 minutes, then dipped in the PAH solution (0.001M, pH 4.3) for 5 minutes, rinsed with ultra-pure water for 1 minute, then dipped in the PAA solution for 5 minutes, rinsed with ultra-pure water for 1 minute. The coated contact lens with PAA/PAH/PAA layer is then dipped in the PAMAM solution (0.001M, pH 4.5) for 5 minutes, rinsed with water for 1 minute, dipped in the PAAm-co-PAA solution (0.001M, pH 4.4) solution for 5 minute, rinsed with water for 1 minute. The above-described dipping and rinsing steps are repeated for about from 10 to 20 times to apply alternatively layers of PAMAM and PAAm-co-PAA with PAAm-co-PAA as the capping layer. The lens is then packaged in saline and sterilized.

Coating B: In a similar coating process, the $2^{nd}$ dip in PAA solution and the $3^{rd}$ dip in PAA solution are omitted.

Coating C: In addition, PAMAM solutions with different pH (from 2.5 to 5.5) and PAAm-co-PAA solutions with different pH (from 2.5 to 4.4) are also used in the above-described coating process.

EXAMPLE 3

Contact Lenses Having Multiple Bilayers of Protasan/PAAm-co-PAA Thereon

PAA and PAAm-co-PAA solutions: PAA and PAAm-co-PAA solutions are prepared as described in Example 2.

Protasan solution: Protasan® is water-soluble chitosan manufactured by Pronova Biomedical. The Molecular weight ranges from about 110,000 to 460,000. A solution of Protasan is prepared by dissolving a suitable amount of the material in water to form a 0.001M Protasan® solution. The concentration is calculated based on the molecular weight of the repeating unit. Once dissolved, the pH of the solution is adjusted by adding 1N hydrochloric acid until a desired pH Coating: A coating having bilayers of Protasan®/PAAm-co-PAA is formed on a soft contact lens made of a fluorosiloxane hydrogel material, lotrafilcori A (CIBA Vision). The contact lens is first dipped in the PAA solution (0.001M, pH2.5) for 30 minutes, then dipped in the Protasan solution (0.001M, pH 3.5, or 4.4, or 5.5) for 5 minutes, rinsed with ultra-pure water for 1 minute, then dipped in the PAAm-co-PAA solution (0.001M, pH 4.4) for 5 minutes, rinsed with ultra-pure water for 1 minute. The 5 minute dipping and 1 minute rinsing steps are repeated for 6 to 20 time to applying alternatively layers of Protasan and PAAm-co-PAA with PAAm-co-PAA as the capping layer. The lens is then packaged in saline and sterilized.

EXAMPLE 4

Contact Lenses Having Bilayers of PAA, Sodium Alginate and PAH

PAA and PAH solutions: PAA and PAH solutions are prepared as described in Example 1.

Sodium Alginate solution: A solution of Sodium Alginate, having a molecular weight of from 100,000 to 400,000 and supplied by Fluka, is prepared by dissolving a suitable amount of the material in water to form a 0.001M Alginate solution. The concentration is calculated based on a molecular weight of the repeating unit of 198.11 g/mol. Once dissolved, the pH of the solution is adjusted by adding 1N hydrochloric acid until a desired pH of 4.5 is reached. The solution is filtered and used immediately, or stored in refrigerator.

Coating: A coating having multiple bilayers of PAA, Sodium Alginate and PAH is formed on a soft contact lens made of a fluorosiloxane hydrogel material, lotrafilcon A (CIBA Vision). The contact lens is first dipped in the PAA solution (0.001M, pH 2.5) for 20 minutes, then rinsed with ultra-pure water three times (2 minutes, 1 minute and 1 minute), then dipped in a PAH solution for 5 minutes, and then rinsed with ultra-pure water three times (for 2 minutes, 1 minute and 1 minute respectively). After applying the first bilayer of PAA and PAH, the above coating procedures are repeated using Sodium Alginate for 5 minutes instead of PAA to apply seven additional bilayers of Sodium Alginate and PAH onto the contact lens. The coated lens is then packaged in saline and sterilized.

EXAMPLE 5

Contact Lenses Having Bilayers of PAA, Sodium Hyaluronate and PAH

PAA and PAH solutions: PAA and PAH solutions are prepared as described in Example 1.

Sodium Hyaluronate solution: A solution of Sodium Hyaluronate, having a molecular weight of from 100,000 to 400,000 and supplied by Lifecore, is prepared by dissolving a suitable amount of the material in water to form a 0.001M Sodium Hyaluronate solution. The concentration is calculated based on a molecular weight of the repeating unit of 198.11 g/mol. Once dissolved, the pH of the solution is adjusted by adding 1N hydrochloric acid until a desired pH of 4.5 is reached. The solution is filtered and used immediately, or stored in refrigerator.

Coating: A coating having multiple bilayers of PAA, Sodium Hyaluronate and PAH is formed on a soft contact lens made of a fluorosiloxane hydrogel material, lotrafilcon A (CIBA Vision). The contact lens is first dipped in the PAA solution (0.001M, pH 2.5) for 20 minutes, then rinsed with ultra-pure water three times (2 minutes, 1 minute and 1 minute), then dipped in a PAH solution for 5 minutes, and then rinsed with ultra-pure water three times (for 2 minutes, 1 minute and 1 minute respectively). After applying the first bilayer of PAA and PAH, the above coating procedures are repeated using Sodium Hyaluronate for 5 minutes instead of PAA to apply seven additional bilayers of Sodium Hyaluronate and PAH onto the contact lens. The coated lens is then packaged in saline and sterilized.

EXAMPLE 6

PAA and PAH solutions: PAA and PAH solutions are prepared as described in Example 1.

Chitosan solution: A solution of Chitosan, having a molecular weight of from 5,000 to 100,000 and supplied by Polyscience, is prepared by dissolving a suitable amount of the material in glacial acetic acid to form a 0.001M Chitosan solution. The concentration is calculated based on a molecular weight of repeating unit of 185.2 g/mol. Once dissolved, the pH of the solution is adjusted by adding acetic acid to 3.2. The solution is filtered and used immediately, or used to prepare a PAH/Chitosan (10:1 solution), then used immediately or stored in refrigerator.

PAH/Chitosan (10:1) solution: A PAH/Chitosan (10:1) solution is prepared by mixing the above prepared PAH and Chitosan solutions at a molar ratio of 10 to 1. After thoroughly mixing, pH is adjusted to pH 4.0. Solution is filtered and used immediately or stored in refrigerator.

Coating: A coating having multiple bilayers of PAA and PAH/Chitosan is formed on a soft contact lens made of a fluorosiloxane hydrogel material, lotrafilcon A (CIBA Vision). The contact lens is first dipped in the PAA solution (0.001M, pH 2.5) for 20 minutes, then rinsed with ultra-pure water three times (2 minutes, 1 minute and 1 minute), then dipped in a PAH/Chitosan solution (pH 4.0) having a molar ratio of 10:1 ([PAH]/[Chitosan]) for 5 minutes, and then rinsed with ultra-pure water three times (for 2 minutes, 1 minute and 1 minute respectively). After applying the first bilayer of PAA and PAH/Chitosan, the above coating procedures are repeated, except that the subsequent PAA dips are 5 minutes in duration, to apply seven additional bilayers of PAA and PAH/Chitosan onto the contact lens. The coated lens is then packaged in saline and sterilized.

EXAMPLE 7

PAA and PAH solutions: PAA and PAH solutions are prepared as described in Example 1.

Chondroitin Sulfate solution: A solution (pH 3.5) of Chondroitin Sulfate, having a molecular weight from 5,000 to 150,000 and supplied by Fluka, is prepared by dissolving a suitable amount of the material in water to form a 0.001M Chondroitin Sulfate solution. The concentration is calculated based on a molecular weight of repeating unit of 514.4 g/mol. Once dissolved, the pH of the solution is adjusted by adding 1N hydrochloric acid to a pH of 3.5. The solution is filtered and used immediately, or stored in refrigerator.

Coating: A coating having multiple bilayers of Chondroitin Sulfate and PAH is formed on a soft contact lens made of a fluorosiloxane hydrogel material, lotrafilcon A (CIBA Vision). The contact lens is first dipped in the PAA solution (0.001M, pH 2.5) for 20 minutes, then rinsed with ultra-pure water three times (2 minutes, 1 minute and 1 minute), then dipped in a PAH solution for 5 minutes, and then rinsed with ultra-pure water three times (for 2 minutes, 1 minute and 1 minute respectively). The coated lens, having a bilayer of PAA and PAH, is dipped in a Chondroitin Sulfate solution (pH 3.5) for 5 minutes, then rinsed with ultra-pure water three times (for 2 minutes, 1 minute and 1 minute respectively), then dipped in a PAH solution for 5 minutes, and then rinsed with ultra-pure water three times (for 2 minutes, 1 minute and 1 minute respectively). About a total of seven bilayers of Chondroitin Sulfate and PAH are applied onto the contact lens. The coated lens is then packaged in saline and sterilized.

EXAMPLE 8

Contact Lenses Having PEI and Bilayers of PAA and PAH/Lactone

PAA Solution: PAA solutions are prepared as described in Example 2:

PAH/Lactone (Polyallylamine-glucone lactone Adduct 1:1): A solution (pH 4.5) of Novartis purified (Polyallylamine-glucone lactone Adduct 1:1) being of a 15.83% liquid concentration, is prepared by adding a suitable amount of the material in water to form a 0.001% PAH/Lactone solution. The concentration is calculated based on the initial concentration of the stock solution. Once dispersed into desired amount of ultra-pure $H_2O$, the pH of the solution is adjusted by adding 1N hydrochloric acid to a pH of 4.5. The solution is filtered and used immediately, or stored in refrigerator.

PEI (Poly(ethyleimine)) solution: A 30% solution of PEI (from Polysciences) having a molecular weight of 70,000 is prepared by dissolving a suitable amount of material in water to form a 0.001M PEI solution. The concentration is calculated based on the average molecular weight of the repeating units. Once dissolved, the pH of the PEI solution is adjusted by adding 1N hydrochloric acid until a desired pH.

Coating: A coating having a pre-coat of PEI (pH 3.5) and multiple bilayers of PAA (pH 2.5) and PAH/Lactone (pH 4.5) is formed on a soft contact lens made of a fluorosiloxane hydrogel material, lotrafilcon A (CIBA Vision). The contact lens is first dipped in the PEI pH 3.5 (0.001M) solution for 5 minutes, then rinsed with ultra-pure water three times (2 minutes, 1 and 1 minute), then dipped in a PAA solution (0.001M, pH 2.5) for 5 minutes, then rinsed with ultra-pure water three times (2 minutes, 1 minute and 1 minute), then dipped in a PAH/Lactone solution (pH 4.5) for 5 minutes, and then rinsed with ultra-pure water three times (for 2 minutes, 1 minute and 1 minute respectively). The bilayers are formed by alternating the lenses between the PAA and PAH/Lactone solutions with respective water rinses until 5 bilayers of PAA and PAH-Lactone are applied onto the contact lens. The coated lens is then packaged in saline and sterilized.

EXAMPLE 9

Bacterial Adherence ATP Assay of Coated Contact Lenses

Contact lenses are often exposed to one or more microorganisms during wear, storage and handling. They can provide surfaces onto which the microorganisms can adhere and then proliferate to form a colony. Microbial adherence to and colonization of contact lenses may enable microorganisms to proliferate and to be retained at the ocular surface for prolonged periods and thereby may cause infection or other deleterious effects on the ocular health of the eye in which the lens is used. Therefore, it is desirous to make various efforts to minimize and/or eliminate the potential for microorganism adhesion to and colonization of contact lenses.

Test lenses are exposed to about 2 ml of about $1.0 \times 10^8$ CFU/ml *P. aeruginosa* GSU #3 (an adherent clinical isolate) in PBS and incubated for about 2 hrs at ~37° C. Lenses are rinsed in PBS to remove cells which, are not firmly attached. ATP is extracted from viable attached cells, Luciferase enzyme is added and light output is measured with a Luminometer A comparable value of Colony Forming Units per the surface area of each test sample ($CFU/mm^2$) is determined by comparison to a concentration curve of the bacterial inoculum.

EXAMPLE 10

Measurements of CoF of Coated Contact Lenses

CoF of a contact lens can be measured by a sled-on-block type of friction tester as follow. Under a certain load (e.g., about 2.0 grams), a contact lens is slid back and forth, at a prescribed speed, against a biologically relevant substrate and both the normal force (N) and the tangential force ($F_T$) are measured. The CoF of the contact lens is calculated based on the equation of $\mu = F_T/N$.

A preferred friction tester comprises: a stationary lens holder assembly, a biologically relevant substrate, a horizontally movable platform, and a plurality of force measuring means.

The stationary lens holder assembly preferably comprises an "A-shaped" holder bracket and a lens holder having a lens-supporting surface. The lens supporting surface of the lens holder has a convex curvature capable of accommodating the back (concave) surface of a contact lens. The lens holder is preferably held by a means in the center of the "A-shaped" holder bracket. The head end of the "A-shaped" stationary sample holder bracket is connected to a first force measuring means (e.g., a load cell from Transducer Techniques) by, for example, a Kevlar® fiber. The two foot-ends of the "A-shaped" holder bracket are connected to nylon string attached with two ½" steel extension springs. The first force measuring means and the steel extension springs are mounted to the frame of the tester.

The horizontally movable platform can be, for example, a table platform (x-table) which moves uniaxially at various speeds and accelerations. The x-table preferably has a dimension of 163 mm long and 19.1 mm wide and can provide a test area having about 140 mm long and about 14.7 mm wide. An example of the x-table is a Model 41 Linear Positioner which is powered by a ZETA Drive Compumotor (Parker Hannifin Corporation), which operates unidirectional at maximum velocities of 1800 mm/min and accelerations of 9000 mm/s².

The biologically relevant substrate can be any material and preferably is a powder-free surgical glove with Biogel® Coating" from Regent®. Preferably, the finger of the glove is cut into a single rectangular strip, and stretched and attached to the x-table by a physical means, for example, jumbo paper clips. Before testing, the substrate attached onto the x-table is lubricated with two drops of a desired lubricant, for example, ultra pure water or Softwear® saline (CIBA vision). Any air between the substrate and the x-table should be removed. The desired lubricant should be applied evenly on the substrate. The substrate should be even and consistent throughout.

Preferably, there are three force-measuring means, a first, a second and a third force-measuring means. Any suitable known force-measuring means can be used. An example is a 100-gram load cells from Transducer Techniques. The first force-measuring means is attached to the sample holder to measure tangential forces (friction forces, $F_T$) in two opposite directions. The second and third force-measuring means reside under the x-table to measure normal forces (N) in the downward direction. The other load cell Values outputted by the normal load cells are converted to grams by a Versatile Amplifier/Conditioner (Transducer Techniques).

Measurements of CoF is performed on the preferred friction tester as follows. A contact lens is placed on a lens holder with the back surface of the contact lens against the lens-supporting surface of the lens hold. The lens holder with the contact lens is assembled with the "A-shaped" holder bracket and then placed in contact with a desired lubricated substrate. This substrate is mounted to a horizontally movable table platform that is capable of moving uniaxially at various speeds and accelerations. About 3 grams of weight is loaded onto the lens holder. This load may represent the force pressed on a contact lens by a blink of eyelids. The three force-measuring means (3 Load cells from Transducer Techniques) measure simultaneously the normal (N) and frictional ($F_T$) forces that are produced from the interaction between the contact lens and the substrate lubricated with a desired lubricant. Multiple data points are taken during a measurement of lubricity/lubricating drag/coefficient of friction of a contact lens. At each data point, CoF $\mu$, is calculated as follows:

$$\mu = F_T/N$$

in which $F_T$ represent actual data reading at each point obtained by the first force measuring means after correcting for the preloading provided by the springs (tangential load cell) during sliding of the substrate against the contact lens and preferably has a unit of gram; N is the sum of $N_1$ and N2; N1 represents actual data reading at each point obtained by the second force-measuring means after correcting for any preloading by the test assembly (normal load cell#1) during sliding of substrate against the contact lens and preferably has a unit of gram; and $N_2$ represents actual data reading at each point obtained by the third force-measuring means after correcting for any preloading by the test assembly (normal load cell#2) during sliding of substrate against the contact lens and has preferably a unit of gram. The average ($\mu_{Ave}$) of all $\mu$'s at every data point will be used to represent the value of CoF of a contact lens.

More preferably, the friction tester further comprises a computer system that controls the tester, collects readings of the normal and tangential forces simultaneously as the biologically-relevant substrate interacts with contact lens, calculates CoF, and records and charts the forces ($F_T$ and N) and CoF ($\mu$) at each data point during testing.

EXAMPLE 11

Measurements of Contact Angles of Coated Contact Lenses

Average contact angles (Sessile Drop) of contact lenses are measured using a VCA 2500 XE contact angle measurement device from AST, Inc., located in Boston, Mass.

EXAMPLE 12

Characterization of Coated Contact Lenses

The contact angle generally measures the surface hydrophilicity of a contact lens. In particular, a low contact angle corresponds to more hydrophilic surface. The contact angles are measured as described in Example 11 and the obtained results are shown in Table 1. The averaged contact angle of a contact lens, which is made of lotrafilcon A and without any coating (LbL or plasma), is about 112 degree. When such contact lens has a surface modification through LbL coating or plasma coating, the averaged contact angle is decreased generally to less than 75 degrees.

COF may be one of parameters that measure the easiness of the on-eye movement of a contact lens. High CoF may increase the likelihood of damaging mechanically the ocular epithelia. The COF is measured as described in Example 10 and obtained results are shown in Table 1. Multiple lenses are measured to obtain the averaged COF. A contact lens without any surface modification (i.e., plasma treatment or LbL coating), which is made of lotrafilcon $A_1$ has an averaged CoF of about 3.72.

Bacterial adhesion on coated contact lenses are characterized according to the procedures described in Example 9 and the obtained results are shown in Table 1.

All results shown in the above examples demonstrate that the lubricious coatings on contact lenses have a high lubricity (characterized by an averaged lubricity/lubricating drag/coefficient of friction of about 3.0 or less and increased hydrophilicity (characterized by an averaged contact angle of less than 80 degrees) while maintaining the desired bulk properties such as oxygen permeability and ion permeability of lens material. Such lenses are useful as extended-wear contact lenses.

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be interchanged either in whole or in part. Therefore, the spirit and scope of the appended claims should not be limited to the description of the preferred versions contained therein.

TABLE 1

Surface Properties of Coated Contact Lenses

| Contact Lenses | Coating Materials | Contact Angle | CoF | Bacterial Adhesion |
|---|---|---|---|---|
| Uncoated Lenses (control) | | 115 | 3.72 | $4.0 \times 10^4$–$3 \times 10^5$ |
| Example 1 | PAA, PAH and PVP | 62 | 2.48 | $4.96 \times 10^3$–$1 \times 10^4$ |
| Example 2 (coating A) | PAA, PAH, PAMAM dendrimer and PAAm-co-PAA | 35 | 2.45 | $1.38 \times 10^4$ |
| Example 3 | PAA, PAAm-co-PAA and Protasan ™ | 30 | 3.17 | $1.55 \times 10^4$ |
| Example 4 | PAA, Sodium Alginate and PAH | 62 | 2.44 | $1.43 \times 10^4$ |
| Example 5 | PAA, Sodium Hyaluronate and PAH | 76 | 3.53 | $1.84 \times 10^5$ |
| Example 6 | PAA, PAH and Chitosan | 36 | 2.73 | $2.39 \times 10^4$ |
| Example 7 | PAA, PAH and Chrondroitin sulfate | 27 | 2.74 | $1.42 \times 10^4$ |
| Example 8 | PAA & PAH-gluconolactone | 50 | 2.37 | $1.92 \times 10^4$ |

What is claimed is:

1. An ophthalmic device, comprising a core material and a lubricious coating,
   wherein said ophthalmic device having said lubricious coating thereon has an increased hydrophilicity characterized by an averaged contact angle of about 80 degrees or less, and wherein said lubricious coating comprises a capping layer of polyvinylpyrrolidone and at least one layer of a lubricious coating material selected from the group consisting of PAMAM dendrimers, PAAm-co-PAA, glycosaminoglycanes, fucoidan, poly-aspartic acid, poly-glutamic acid, carboxymethyl cellulose, carboxymethyl dextranes, alginates, pectins, gellan, carboxyalkyl chitins, carboxymethyl chitosans, sulfated polysaccharides, glucoproteins, and aminoalkylated polysaccharides.

2. The ophthalmic device of claim 1, wherein said ophthalmic device is a contact lens.

3. A contact lens of claim 2, wherein said core material is a hydrogel.

4. A contact lens of claim 3, wherein said hydrogel is a siloxane-containing polymer.

5. The ophthalmic device of claim 2, wherein said lubricious coating further comprises at least one layer of a polyionic material which is non-covalently bond to the lubricous material.

6. The ophthalmic device of claim 2, wherein said contact lens has an averaged CoF of about 3.0 or less.

7. The ophthalmic device of claim 2, wherein said contact lens has increased bacterial adhesion resistance.

8. The ophthalmic device of claim 7, wherein said contact lens has increased bacterial adhesion resistance characterized by having a value of Colony Forming Units (CFU/mm$^2$) per the surface area which is at least about one order lower than value of Colony Forming Units (CFU/mm$^2$) per the surface area of an uncoated contact lens, wherein said contact lens having said lubricious coating and the uncoated contact lens are made of same core material.

9. A ophthalmic device, comprising a core material and a lubricious coating, wherein said ophthalmic device having said lubricious coating thereon has an increased hydrophilicity characterized by an averaged contact angle of about 80 degrees or less, wherein said lubricious coating comprises a capping layer of polyvinylpyrrolidone or at least one layer of a lubricious coating material selected from the group consisting of PAMAM dendrimers, PAAm-co-PAA, glycosaminoglycanes, fucoidan, poly-aspartic acid, poly-glutamic acid, carboxymethyl cellulose, carboxymethyl dextranes, alginates, pectins, gellan, carboxyalkyl chitins, carboxymethyl chitosans, sulfated polysaccharides, glucoproteins, and aminoalkylated polysaccharides, and wherein said lubricious coating further comprises at least one layer of a polyionic material which is non-covalently bond to the lubricous material.

10. The ophthalmic device of claim 9, wherein said lubricious coating comprises a plurality of lubricious bilayers each composed of, in no particular order, one layer of the lubricious material and one layer of the polyionic material.

11. The ophthalmic device of claim 10, wherein the number of the plurality of the lubricious bilayers is from 2 to 20.

12. The ophthalmic device of claim 11, wherein the number of the plurality of the lubricious bilayers is from 4 to 10.

13. The ophthalmic device of claim 9, wherein the lubricious coating further comprises a capping layer of polyvinylpyrrolidone.

14. The ophthalmic device of claim 9, wherein said ophthalmic device is a contact lens having an averaged CoF of about 3.0 or less.

15. The ophthalmic device of claim 9, wherein said ophthalmic device is a contact lens having increased bacterial adhesion resistance.

16. The ophthalmic device of claim 14, wherein said contact lens has increased bacterial adhesion resistance characterized by having a value of Colony Forming Units ($CFU/mm^2$) per the surface area which is at least about one order lower than value of Colony Forming Units ($CFU/mm^2$) per the surface area of an uncoated contact lens, wherein said contact lens having said lubricious coating and the uncoated contact lens are made of same core material.

17. A contact lens of claim 9, wherein said core material is a hydrogel.

18. A contact lens of claim 16, wherein said hydrogel is a siloxane-containing polymer.

19. A ophthalmic device, comprising a core material and a lubricious coating, wherein said ophthalmic device having said lubricious coating thereon has an increased hydrophilicity characterized by an averaged contact angle of about 80 degrees or less, and wherein said lubricious coating comprises at least one layer of a lubricious coating material selected from the group consisting of alginates, PAH lactone, hyaluronic acid and salts thereof, PAMAM dendrimers, PAAm-co-PAA, chondroitin sulfate, chitosan, proteoglycans, and mixtures thereof.

20. The ophthalmic device of claim 19, wherein said ophthalmic device is a contact lens.

21. The ophthalmic device of claim 19, wherein said lubricious coating comprises a capping layer of polyvinylpyrrolidone.

\* \* \* \* \*